United States Patent [19]

Ziegler et al.

[11] Patent Number: 4,995,957

[45] Date of Patent: Feb. 26, 1991

[54] DEVICE AND METHOD FOR THE ELECTROPHORETIC SEPARATION OF MACROMOLECULES

[76] Inventors: Andreas Ziegler, Steinweg 37, 3550 Marburg; Karl-Heinz Geiger, Weissdornweg 13, 7400 Türbingen, both of Fed. Rep. of Germany

[21] Appl. No.: 191,689

[22] Filed: May 9, 1988

[30] Foreign Application Priority Data

May 7, 1987 [DE] Fed. Rep. of Germany ....... 3715170

[51] Int. Cl.⁵ .................. G01N 27/26; B01D 57/62
[52] U.S. Cl. .................. 204/182.8; 204/299 R; 204/300 R
[58] Field of Search ............ 204/182.8, 299 R, 180.1, 204/182.1, 300 R

[56] References Cited

FOREIGN PATENT DOCUMENTS

87/02133  4/1987  PCT Int'l Appl. ............ 204/299 R

Primary Examiner—John F. Niebling
Assistant Examiner—John S. Starsiak, Jr.
Attorney, Agent, or Firm—Evenson, Wands, Edwards, Lenahan & McKeown

[57] ABSTRACT

An electrophoretic separation apparatus suitable for the separation of macromolecules is provided. Electrode elements are provided for generating an electric field for acting on a specimen. Rotating elements are provided for rotating the electrode elements with respect to the specimen. Using this invention, the orientation of the electric field between the electrodes is changed by the rotation of the electrode elements. This arrangement provides a high separating efficiency in a short period of operation. A method for electrophoretic separation of macromolecules is also provided.

19 Claims, 2 Drawing Sheets

DEVICE AND METHOD FOR THE ELECTROPHORETIC SEPARATION OF MACROMOLECULES

BACKGROUND AND SUMMARY OF THE INVENTION

The invention relates to an electrophoresis device and an electrophoresis method for the separation of macromolecules and the use of this device.

Electrophoresis devices are known for separating macromolecules from a substance, for example, separating polypeptides or nucleic acids, where the separation takes place according to the molecular weight or the structural characteristics.

Recently, methods have also become known which permit the separating of very large nucleic acid molecules or even intact chromosomal deoxyribonucleic acid (DNA), for example, of yeast cells (Saccharomyces cerevisiae). These methods include, for example, the "Pulsed Field Gel Electrophoresis" (PFGE) described, for example, in U.S. Pat. No. 4,473,452, and the "Orthogonal Field Alternation Gel Electrophoresis" (OFAGE) described by Carle & Olson in *Nucl Acids Res.* 12, 5647-5664, 1984).

It is also possible to use these methods for the analysis of chromosomal fragments, for example, of the human (Ragoussis et al, *EBs Lett.* 204, 1-4, 1986; Lawrance et al, *Science* 235, 1387-1390, 1987).

Both the PFGE and the OFAGE utilize the fact that large nucleic acid molecules apparently must first orient themselves in an electric field before they will be able to start travelling. The duration of this orientation phase is probably directly proportional to the length of the nucleic acid molecules (Smith et al, "Meth. Enzymol.", in the printing process, 1987). In the PFGE and the OFAGE, two non-homogeneous electric fields, alternating at an obtuse angle (via electronic circuits), act upon the macromolecules. As a result, in an alternating manner, the macromolecules must first reorient themselves in the one electric field and then in the second electric field before they can travel in the direction of the respective anode. However, a significant disadvantage of this method is the fact that the field intensities of the two non-homogeneous fields are identical only for the specimen located in the center. As a result, it is difficult to compare the mobilities of macromolecules in different specimens. In addition, according to these systems, the duration of a typical electrophoresis experiment is 40-72 hours (compare FIG. 1 in Lawrance et al, *Science* 235, 1387-1390, 1987).

Experiments addressing these difficulties are also known from literature. Chu et al (*Science* 234, 1582-1686, 1986) describe a modification ("Contour-Clamped Homogeneous Electric Fields") of the OFAGE which uses a hexagonal electrophoresis apparatus, the multiple electrodes of which are connected with one another via resistors. Although this electrophoresis method results in a good comparability of the mobility of macromolecules of different specimens, it requires extraordinarily large electrophoresis apparatuses when using the standard size (20×20 cm) agarose gels. These apparatuses are difficult to manufacture and also have considerable disadvantages with respect to cooling and the electric power supply.

Although in the case of a "Field Inversion Gel Electrophoresis" (Carle et al, *Science* 232, 65-68, 1986), the electrophoresis is carried out in conventional apparatuses with one cathode and one anode, the direction of the current is switched electronically from time to time. This results in the desired reorientation of the macromolecules. However, this method also has disadvantages because the dissolution process is not high, and the mobility of the nucleic acid molecules depends considerably on the concentration. In addition, the platinum electrodes corrode very rapidly.

A method is also known in which the gel, together with the macromolecules to be separated, rotate in a homogeneous electric field (Anand, *Trends Genet.* 2, 278-283, 1986). According to this method, it is difficult to steer the heavy gel table with the gel. Further, the required duration of these known electrophoresis methods is one weak and longer. Gels with very low agarose concentrations which allow the separation of DNA molecules with more than 1,000,000 base pairs, do not have the stability that is necessary for an efficient separation of the nucleic acid molecules in the course of this extreme duration.

An object of the present invention is to provide a device and a method which maintain the advantages of the methods discussed above, and which provide a particularly rapid and reproduceable separation of macromolecules from several specimens in a gel located in a buffer solution. Another object is to also provide an electrophoresis apparatus and method which provide an excellent comparability of the mobility without requiring expensive equipment for electronic switching processes or very costly electrophoresis apparatuses.

These objects and other objects are achieved by providing an electrophoretic separation apparatus suitable for the separation of macromolecules. The apparatus includes electrode elements which generate a electric field. The electrode elements can be rotated by rotating driving elements which rotate the electrode elements with respect to at least one specimen. A method corresponding to this apparatus is also provided.

This apparatus and method provide an excellent separation of macromolecules in an extremely short duration. Further, using the present invention, the electrophoresis device does not require an extremely large size as known apparatuses which have been used for the separation of macromolecular DNAs. This system is relatively inexpensive and is of simple construction and operation when compared to the known devices.

Other objects, advantages and novel features of the present invention will become apparent from the following detailed description of the invention when considered in conjunction with the accompanying drawings.

DETAILED DESCRIPTION OF THE DRAWINGS

The electrophoresis device according to the present invention includes a lower part which may correspond to that of conventional apparatuses for carrying out horizontal gel electrophoreses. The lower part contains an electrophoresis buffer and the gel medium. It is particularly important that the electrophoresis buffer can be circulated and cooled.

Figure 1:
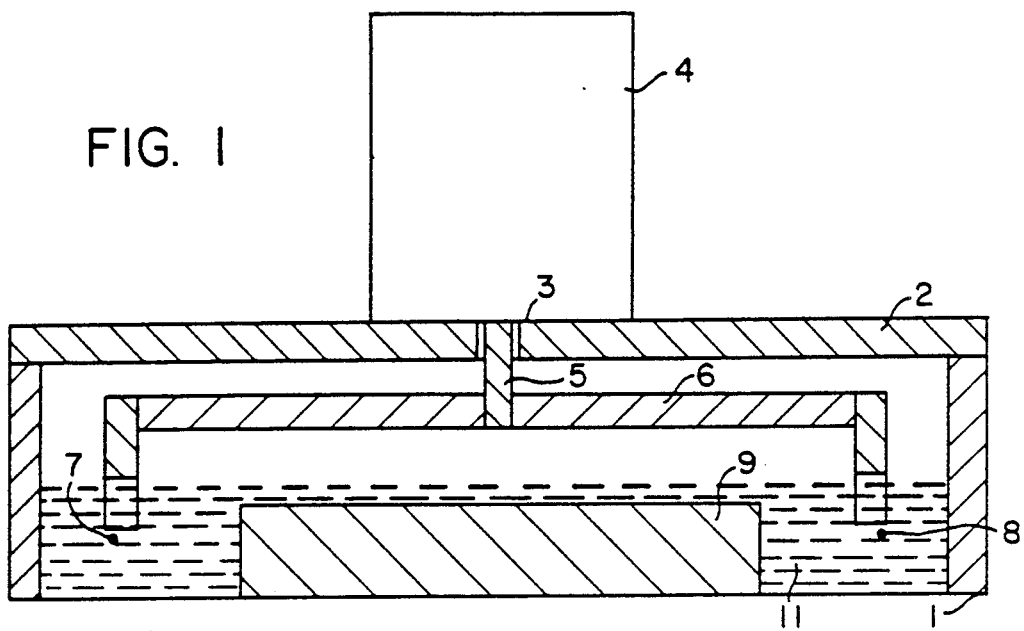
FIG. 1 is a cross-sectional side view of an electrophoresis device according to certain preferred embodiments of the present invention.
Figure 2:
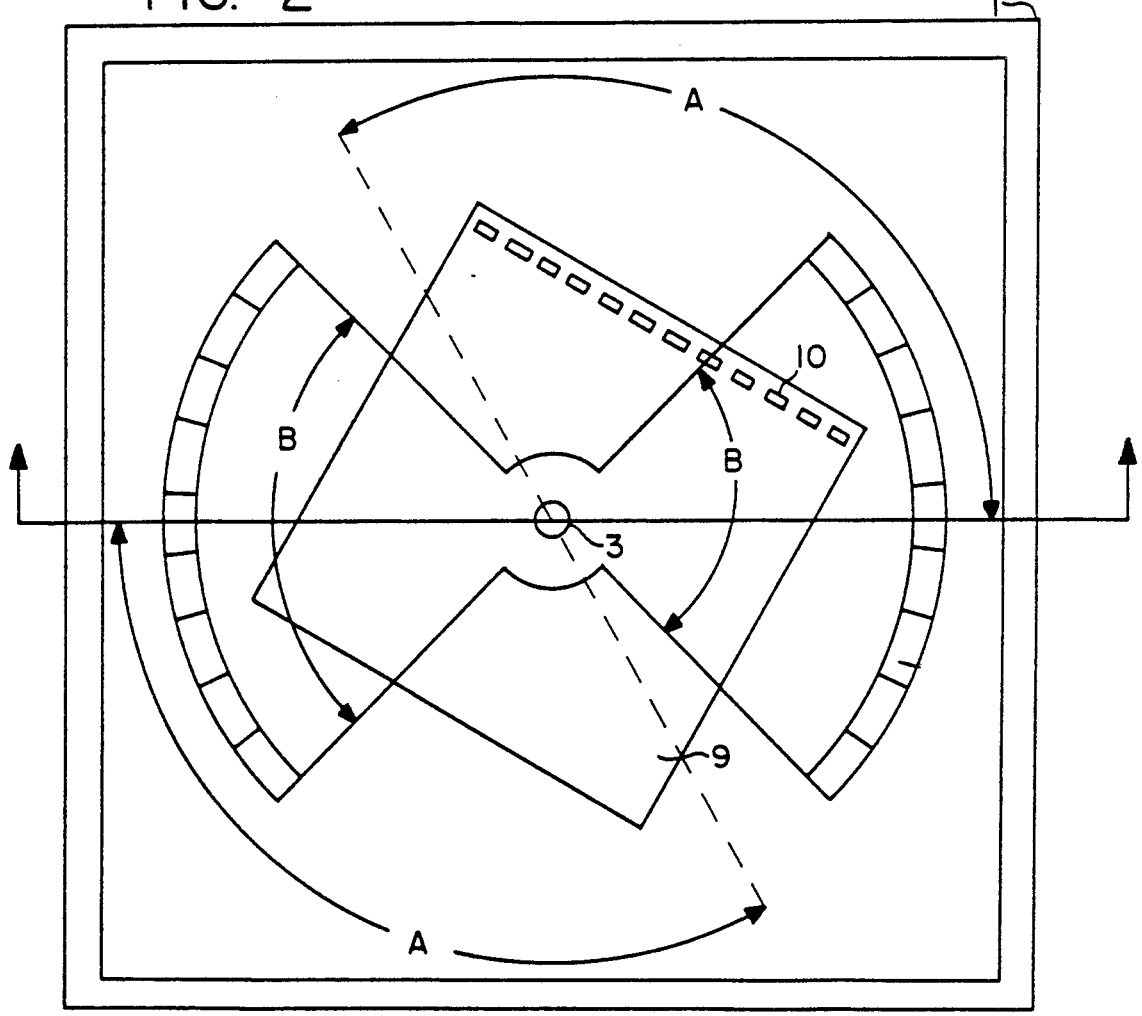
FIG. 2 is a top view of the device shown in FIG. 1.

As shown in FIGS. 1 and 2, an upper part 1 that cooperates with the lower part includes a lid 2 having an aperture (drilled hole) 3. On the lid 2, a controllable motor 4 is mounted. The motor includes a shaft 5 which extends through the aperture 3 of the lid 2. At a lower end of the shaft 5, an electrode carrying device 6 is disposed which has two electrodes 7, 8 fastened thereto. A rotation of the motor shaft over the pivot angle A results in a rotation of the electrode carrier device over the angle A and thus simultaneously in a rotation of the homogeneous electric field over angle A. This angle can be any dimension, and according to certain preferred embodiments is about 90° to 150°.

In apparatuses that are to be used for a comparison of the mobility of macromolecules of different specimens according to certain preferred embodiments of the invention, it is a special advantage for the electrodes 7, 8 to be arranged in a curved manner. The anode 7 and the cathode 8 each have the shape of circular arcs, and have identical center angles B. In addition, in certain preferred embodiments, it is preferred for the curved electrodes to be precisely opposite one another in order to form a homogeneous electric field.

The medium, such as an agarose gel 9, is of the type suitable for the separation of macromolecules and contains the specimens to be separated. It is contemplated that the agarose gel 9 be prepared in agarose blocks according to U.S. Pat. No. 4,473,452 or one of the above-mentioned other publications. Thus, the agarose blocks include correspondingly shaped wells (pits or shafts) 10. The specimens are inserted into the wells 10. According to certain preferred embodiments, the specimen is preformed into insert blocks which can be placed into the wells 10. The gel is disposed in a buffer solution 11.

Figure 3:
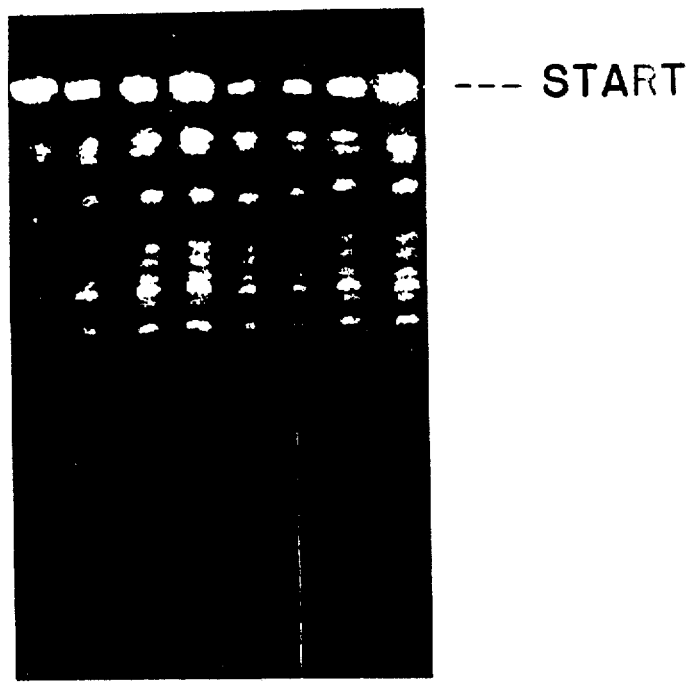
FIG. 3 is an example of the result of a typical electrophoresis experiment using the present invention.

With reference to FIG. 3, a typical electrophoresis experiment will be described in Example I, using the above-explained electrophoresis device. As an example, chromosomal DNAs of yeast (Saccharomyces cerevisiae, WAY 5-4A Strain) were separated in this experiment. Naturally, deviations are possible from the experimental parameters selected here. This example is offered by way of illustration only and should not be construed as limiting the scope of the present invention in any way.

EXAMPLE 1

The electrophoresis is carried out for 21 hours in 0.25×Tris-Borate EDTA buffer (1×TBE is 90 mM tris, 90 mM boric acid, 2.5 mM EDTA with a pH-value of 8.2) at 8° C., and a constant voltage of 110 v direct current with circular-arc-shaped electrodes (spacing 19 cm) is applied. The macromolecules are separated in a 1% agarose gel (13.5×13.5 cm). In this case, the electrode carrier device is moved forward and/or backward every 90 seconds around the angle of rotation (in this case, 120°). After the conclusion of the electrophoresis, the separated DNA-molecules are made visible by ethidium bromide and UV-light (302 nm).

A characteristic separation is shown in FIG. 3. "Start" shows the position of the small blocks of chromosome DNAs of yeast that were inserted into the wells of the gel. Under the mentioned conditions, in the case of the WAY 5-4A yeast strain, 12–14 intact chromosomal DNA-molecules with lengths of 250–2,000 kilo base pairs can be separated from one another, in which case the macromolecules of different specimens can be excellently compared with one another.

The main problems of the PFGE and OFAGE experiments can be avoided by means of the electrophoresis method according to the present invention. The typical experiment according to the present invention requires an unusually short duration of only 21 hours, and nevertheless results in an excellent separation of the chromosomal DNA-molecules. By means of the electrophoresis device according to the present invention, it is also possible to separate much smaller or even larger DNA-molecules than those shown in FIG. 3. In addition, it is possible to excellently separate macromolecules in a standard size gel (20×20 cm) while utilizing the whole gel surface, with an electrophoresis device that requires a total of lateral measurements of only approximately 35×35 cm. Compared to the conventional apparatuses suited for the separation of macromolecular DNAs, particularly to that described by Chu et al, in Science 234, 1582–1586, 1986, the present invention provides considerable progress so that an industrial use of this invention is not prevented or hindered and is totally practicable. In addition, the control of the motor connected with the electrode carrier device is very simple and cost-effective, in comparison to the electronic switching system in the case of the PFGE and other systems discussed above.

Summarizing, it may be stated that the device of the present invention solves the above-mentioned problems of known devices and methods during the electrophoretic separation of macromolecules, and thus leads to a decisive improvement and simplification of the existing electrophoresis methods.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. Electrophoretic separation apparatus suitable for the separation of macromolecules, comprising:
   electrode means for generating an electric field for acting on at least one specimen;
   electrode carrier means for holding said electrode means; and
   rotating driving means for rotating said carrier means and said electrode means with respect to the at least one specimen.

2. Apparatus as in claim 1, wherein said rotating driving means includes a controllable motor for rotating said carrier means and said electrode means around an axis.

3. Apparatus as in claim 2, wherein said electrode means include two electrodes arranged opposite one another with respect to said axis on said carrier means.

4. Apparatus as in claim 3, wherein said two electrodes each have a semi-circular arc configuration, include a common center point of curvature and are disposed on a common circular plane.

5. Apparatus as in claim 4, wherein said two electrodes have identical arc angles and identical radii and are arranged symmetrically with respect to said common center point of curvature.

6. Electrophoretic separation apparatus suitable for the separation of macromolecules comprising:

electrode means for generating an electric field influencing a specimen;

rotating means for rotating said electrode means with respect to the specimen.

7. Apparatus as in claim 6, wherein said electrode means include two electrodes each in the configuration of an arc, said two electrodes having a common center point of curvature and being oppositely spaced from said common center point.

8. Apparatus as in claim 7, wherein said two electrodes have an identical arc angle from said center point of curvature.

9. Apparatus as in claim 8, wherein said two electrodes are disposed on a common circular plane and are symmetrical with respect to said common center point.

10. Apparatus as in claim 9, wherein said rotating means rotates said electrode means in an intermittent, oscillatory manner over an angle of about 90° to 150°.

11. Apparatus as in claim 9, further including an electrode carrYing means for holding said two electrodes.

12. Apparatus as in claim 11, wherein said rotating means rotates said carrying means.

13. Apparatus as in claim 12, wherein said rotating means is a controlled motor connected to said carrying means.

14. Method for electrophoretic separation of macromolecules, comprising:

subjecting at least one specimen to an electric field generated between electrode means;

intermittently changing the orientation of the electric field by rotating the electrode means with respect to the at least one specimen.

15. Method as in claim 14, wherein said changing of the orientation of the electric field includes using a carrying means to which the electrode means are fastening, said rotating including rotating said carrying means.

16. Method as in claim 15, wherein said subjecting of the at least one specimen to the electric field includes using two electrodes each being in the configuration of an arc, said two electrodes being disposed on a common circular plane and having a common center, said two electrodes having identical radii, identical arc angles from said center point and being disposed opposite one another symmetrically with respect to the center point.

17. Method as in claim 16, wherein said rotating includes intermittently rotating the electrode means over a pivot angle, said angle being varied during certain rotation periods.

18. Method as in claim 16, wherein said subjecting of the at least one specimen to the electric field includes using at least one specimen disposed in a gel located between the two electrodes, the gel being in contact with a buffer solution having an electrophoretic separating temperature and the buffer solution being circulated, said electrode means being immersed in said buffer solution.

19. Method as in claim 14, wherein said subjecting of the at least one specimen to the electric field includes using at least one specimen from which at least one of the following macromolecules is separated: nucleic acids, polypeptides, chromosomes, chromosome fragments, molecules, organelles, cells, groups of molecules, groups of organelles and groups of cells; of at least one of the following origins: human, animal, plant, prokaryote and virus.

* * * * *

UNITED STATES PATENT AND TRADEMARK OFFICE
CERTIFICATE OF CORRECTION

PATENT NO. : 4,995,957

DATED : February 26, 1991

INVENTOR(S) : Andreas Ziegler; Karl-Heinz Geiger

It is certified that error appears in the above-identified patent and that said Letters Patent is hereby corrected as shown below:

On the title page item

[76]  Change "Turbingen" to -- Tubingen --.

Column 1, line 28, change "EBs" to -- FEBS --.
Column 2, line 16, change "weak" to -- week --.
Column 2, line 35, change "a" to -- an --.

Claim 3, line 2, change "include" to -- includes --.
Claim 7, line 2, change "include" to -- includes --.
Claim 11, line 2, change "carrYing" to -- carrying --.

Please add Figure 3 to the patent, attached hereto.

Signed and Sealed this

Twenty-seventh Day of August, 1991

Attest:

HARRY F. MANBECK, JR.

Attesting Officer

Commissioner of Patents and Trademarks